United States Patent
Ambrose

(10) Patent No.: US 9,795,572 B2
(45) Date of Patent: Oct. 24, 2017

(54) METHOD FOR SHORTENING ANTI-INFECTIVE THERAPY DURATION IN SUBJECTS WITH INFECTION

(71) Applicant: INSTITUTE FOR CLINICAL PHARMACODYNAMICS, INC., Latham, NY (US)

(72) Inventor: Paul G. Ambrose, Latham, NY (US)

(73) Assignee: INSTITUTE FOR CLINICAL PHARMACODYNAMICS, INC., Schenectady, NY (US)

(*) Notice: Subject to any disclaimer, the term of this patent is extended or adjusted under 35 U.S.C. 154(b) by 0 days.

(21) Appl. No.: 14/912,189

(22) PCT Filed: Jan. 26, 2016

(86) PCT No.: PCT/US2016/014850
§ 371 (c)(1),
(2) Date: Feb. 16, 2016

(87) PCT Pub. No.: WO2016/123063
PCT Pub. Date: Aug. 4, 2016

(65) Prior Publication Data
US 2017/0065539 A1    Mar. 9, 2017

Related U.S. Application Data

(60) Provisional application No. 62/107,740, filed on Jan. 26, 2015, provisional application No. 62/267,442, filed on Dec. 15, 2015.

(51) Int. Cl.

| | | |
|---|---|---|
| A61K 31/195 | (2006.01) |
| A61K 31/47 | (2006.01) |
| A61K 31/34 | (2006.01) |
| A61K 31/24 | (2006.01) |
| A61K 31/137 | (2006.01) |
| A61K 45/06 | (2006.01) |
| A61K 31/375 | (2006.01) |
| A61K 31/5383 | (2006.01) |
| A61K 33/14 | (2006.01) |
| A61K 31/165 | (2006.01) |
| A61K 31/5365 | (2006.01) |

(52) U.S. Cl.
CPC .......... *A61K 31/137* (2013.01); *A61K 31/165* (2013.01); *A61K 31/375* (2013.01); *A61K 31/5365* (2013.01); *A61K 31/5383* (2013.01); *A61K 33/14* (2013.01); *A61K 45/06* (2013.01)

(58) Field of Classification Search
CPC .. A61K 31/137; A61K 31/165; A61K 31/375; A61K 31/5365; A61K 31/5383
USPC ................................ 514/567, 311, 474, 538
See application file for complete search history.

(56) References Cited

U.S. PATENT DOCUMENTS 3,067,099 A * 12/1962 McCormick ........... C07K 9/008
424/115

FOREIGN PATENT DOCUMENTS

| WO | 00/66120 | 11/2000 |
| WO | 2006/071685 | 7/2006 |

OTHER PUBLICATIONS

Lyte et al., "Catecholamine Induced Growth of Gram Negative Bacteria", Life Sciences, vol. 50, No. 3, pp. 203-212 (1992).*
Ciaffi et al., "Various Antibiotics ' Antibacterial Activity Against Recently Isolated Gram-Negative Microbe Strains", Antibiotica, VO. 6, No. 4, pp. 241-248 (1968).*
International Search Report dated Apr. 7, 2016 in corresponding International Application No. PCT/US16/14850.

* cited by examiner

*Primary Examiner* — Kevin E Weddington
(74) *Attorney, Agent, or Firm* — Wenderoth, Lind & Ponack, L.L.P

(57) ABSTRACT

Methods of shortening the duration of anti-infective therapy and increasing the effectiveness of anti-infective drugs in subjects with infection are present. The methods are based on altering the replication rate of a pathogen, which makes the pathogen more susceptible to the actions of the anti-infective drug.

23 Claims, 6 Drawing Sheets

METHOD FOR SHORTENING ANTI-INFECTIVE THERAPY DURATION IN SUBJECTS WITH INFECTION

BACKGROUND OF INVENTION

A major challenge in treating infectious diseases is the duration of anti-infective therapy required to eradicate the infecting pathogen. Diseases like acute otitis media, urinary tract infections, and skin and skin-structure infections are often only effectively treated with anti-infective agents when the agents are administered for a number of days. Infections like endocarditis, bone and joint infections, and infections associated with biofilms can require many weeks of treatment, while tuberculosis and leprosy often require anti-infectives for several months, or more.

The major reason for the wide-range in therapy duration for different infectious diseases is the rate of pathogen replication. The nature of some pathogens is to replicate slowly while for others, their replication rate is environment dependent. Mycobacterium such as *Mycobacterium tuberculosis* and *M. leprae* replicate very slowly. The replication rate of staphylococci, streptococci and Gram-negative bacilli is rapid in some environments (e.g., lung parenchyma) but slow in other environments (e.g., within a biofilm or cardiac vegetation).

A large number of anti-infective agents are only active against a pathogen during replication. Therefore, for many of those pathogens that replicate slowly, a prolonged course of treatment is required to achieve complete eradication of the pathogen from the host.

Prolonged duration of anti-infective therapy increases the patient's risk of drug-related toxicity, increases the probability for drug-resistance selection, and decreases the likelihood that a patient will receive a complete course of therapy. Each of these outcomes can have profound societal costs, not only in terms of increased patient morbidity and mortality, but also in the increased consumption of scarce healthcare resources. Therefore, there is an urgent need for means of achieving treatment of infectious diseases that typically require a long duration of anti-infective therapy, while at the same time decreasing treatment duration.

BRIEF SUMMARY OF INVENTION

The present invention is directed to the novel and unexpected finding that modulation of pathogen replication can be used to decrease treatment duration in some infectious diseases that typically require a long duration of anti-infective therapy. A primary goal of anti-infective therapy is to eradicate the infecting pathogen as rapidly as possible. One way to shorten the duration of anti-infective therapy is to make the pathogen more vulnerable to the killing actions of anti-infective agents. Given that the rate of pathogen eradication is linked to pathogen replication rate, it follows that modulating pathogen replication in the context of effective anti-infective drug(s) exposure alters therapy duration.

Presented here are methods based on one or more of (i) shortening anti-infective therapy duration and (ii) increasing the effectiveness of anti-infective drugs in subjects with infection by changing the pathogen's replication rate. These methods include administering to a subject an agent or agents that modulate the infecting pathogen's replication rate in the context of effective anti-infective drug(s) exposure.

Thus, and in a first aspect, the invention is directed to methods of treating an infectious disease in a subject, comprising administering to a subject having an infectious disease (i) a first agent that alters the replication rate of a pathogen causing the infectious disease and (ii) a second agent that is an anti-infective against the pathogen causing the infectious disease.

In a second aspect, the invention is directed to methods of shortening duration of infectious disease treatment in a subject, comprising administering to a subject having an infectious disease (i) a first agent that alters the replication rate of a pathogen causing the infectious disease and (ii) a second agent that is an anti-infective against the pathogen causing the infectious disease.

In a third aspect, the invention is directed to methods of increasing effectiveness of an anti-infective treatment of an infectious disease in a subject, comprising administering to a subject having an infectious disease (i) a first agent that alters the replication rate of a pathogen causing the infectious disease and (ii) a second agent that is an anti-infective against the pathogen causing the infectious disease.

In certain embodiments of each aspect of the invention, the first agent increases the replication rate of the pathogen. In certain embodiments of each aspect of the invention when the pathogen is a bacterium, the first agent may be one or more compounds comprising an aromatic ring with two adjacent hydroxyl groups, such as a catechol moiety or a 3,4-dihydroxyfuran moiety. Examples of compounds comprising a catechol moiety include, but are not limited to a catecholamine. In specific examples, the first agent includes, but is not limited to, one or more compounds selected from the group consisting of Dopamine, Norepinephrine, Nordefrin, Levodopa, Levonordefrin (Corbadrine), Methyldopa, Isoetharine, Isoproterenol, Carbidopa, Epinephrine, Methyldopate, Dobutamine, Droxidopa and Ascorbic Acid.

In certain embodiments of each aspect of the invention when the pathogen is a bacterium, the second agent is one or more compounds antibiotics. Examples of antibiotics include, but are not limited to, a glycopeptide, a rifamycin, a sulfonamide, a beta-lactam, a tetracycline, an amphenicol (such as chloramphenicol), an aminoglycoside, a macrolide, a streptogramin, a quinolone, a fluoroquinolone, an oxazolidinone and a lipopeptide. Specific examples of antibiotics include, but are not limited to, tetracycline, tigecycline, minocycline, oxazolidinone antibacterial agents, aminoglycoside antibacterial agents, quinolone antibacterial agents, vancomycin, teicoplanin, eremomycin, oritavancin, chloroeremomycin, and daptomycin.

In each aspect of the invention, the first agent and the second agent are administered to the subject sequentially or concurrently, and when administered sequentially the agents may be administered in either order.

In certain embodiments of each aspect of the invention, the infectious disease is a bacterial infection, a viral infection or a fungal infection. Examples of bacterial infections include, but are not limited to, otitis media, a urinary tract infection, a skin and skin-structure infection, pneumonia, endocarditis, a bone and/or joint infection, an infection associated with a biofilm, tuberculosis, or leprosy.

In certain embodiments of each aspect of the invention, the pathogen is a bacterium, a fungus, or a virus. Examples of bacteria include, but are not limited to, a mycobacterium, a species of staphylococci, a species of streptococci, or a Gram-negative bacilli. Specific examples include, but are not limited to, *Mycobacterium tuberculosis, M. leprae, Staphylococcus aureus, Streptococcus pneumoniae,* and *Escherichia coli.*

In each aspect of the invention, the subject is human, a non-human primate, bird, horse, cow, goat, sheep, a dog, cat, or rodent.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

DETAILED DESCRIPTION OF THE INVENTION

I. Definitions

Figure 1:
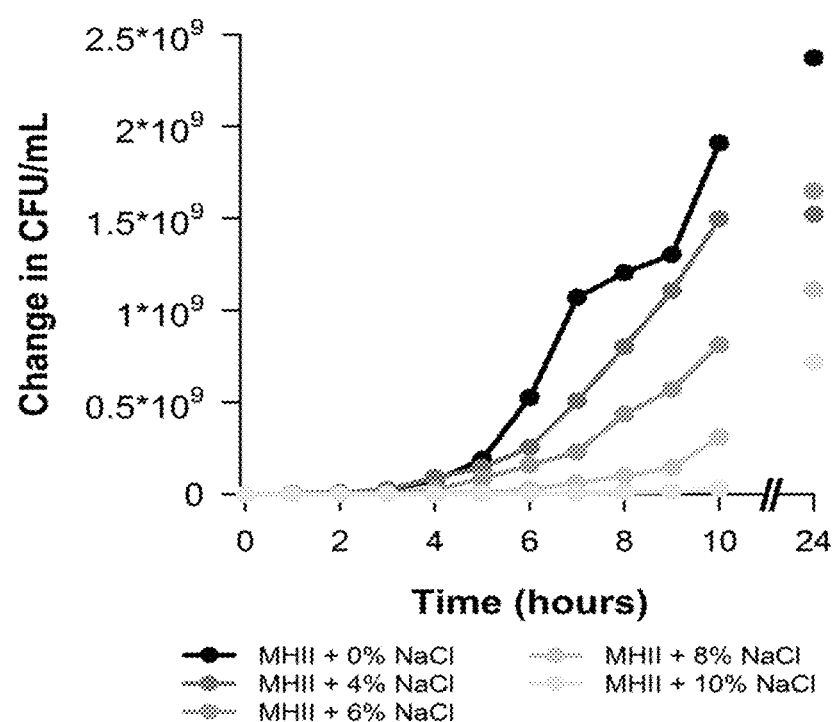
FIG. 1 shows the impact of sodium chloride concentration on *S. aureus* ATCC 29213 growth rate in Mueller-Hinton II broth media.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

As indicated above, the methods of the invention are based on increasing the susceptibility of a pathogen causing an infectious disease to the effects of an anti-infective by modifying the replication rate of the pathogen. Such methods can both shorten the required duration of anti-infective therapy and increase the effectiveness of an anti-infective drug in a subject with infection.

Each of the methods provided herein is based on altering the replication rate of a pathogen causing the infectious disease. In the first aspect, the invention is directed to methods of treating an infectious disease in a subject. In the second aspect, the invention is directed to methods of shortening duration of infectious disease treatment in a subject. In the third aspect, the invention is directed to methods of increasing effectiveness of an anti-infective in treatment of an infectious disease in a subject. Each of these three aspects comprise administering to a subject having an infectious disease (i) a first agent that alters the replication rate of a pathogen causing the infectious disease and (ii) a second agent that is an anti-infective against the pathogen causing the infectious disease.

The change in replication rate may be an increase in replication rate. Alternatively, change in replication rate may be a decrease in replication rate. The change in replication rate may be short term (several hours) or long term in duration (several days). Onset of the change in replication rate may be immediate or it may be delayed. The change in replication rate may be gradual or it may be instantaneous. The replication rate may be altered, whether as an increase or a decrease, by a percentage of at least about 5, 10, 15, 20, 25, 30, 35, 40, 45, 50, 55, 60, 65, 70, 75, 80, 85, 90, or 95, or more, compared to the replication rate of the same pathogen, under the same or similar conditions, that is not exposed to the first agent.

The first agent may be any compound or compounds that change the replication rate of the pathogen, whether it is an increase or a decrease in replication rate. When the pathogen is a bacteria, exemplary compounds comprise an aromatic ring with two adjacent hydroxyl groups, such as a catechol moiety or a 3,4-dihydroxyfuran moiety. Examples of acceptable compounds comprising catechol moieties include catecholamines. In specific examples, the first agent includes, but is not limited to, one or more compounds selected from Table 1.

TABLE 1
| Compound | Structure |
|---|---|
| Dopamine | 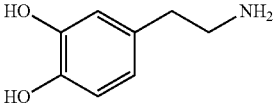 [SMILES: NCCc1ccc(O)c(O)c1] |
| Norepinephrine | 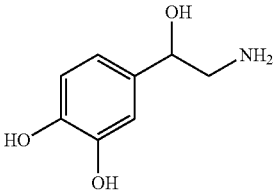 [SMILES: NCC(O)c1ccc(O)c(O)c1] |
| Nordefrin | 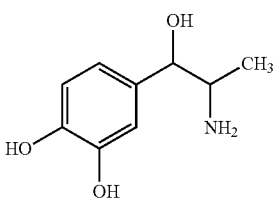 |
| Levodopa | 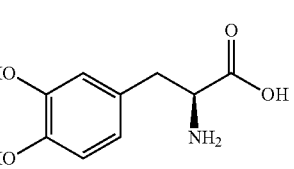 |
| Levonordefrin (Corbadrine) | 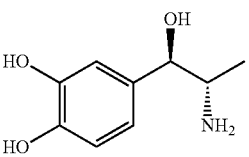 |
| Methyldopa | 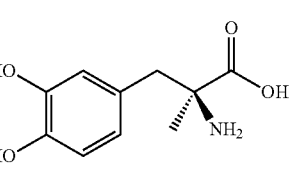 |
| Isoetharine | 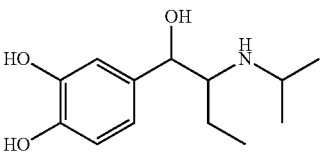 [SMILES: CCC(NC(C)C)C(O)c1ccc(O)c(O)c1] |
| Isoproterenol | 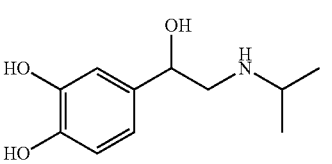 |
| Carbidopa | 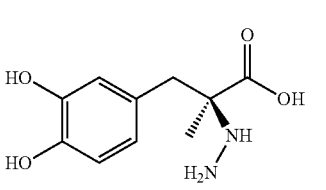 |

TABLE 1-continued

| Compound | Structure |
| --- | --- |
| Epinephrine | *(structure)* |
| Methyldopate | *(structure)* |
| Dobutamine | *(structure)* |
| Droxidopa | *(structure)* |
| Ascorbic acid (Vitamin C) | *(structure)* |

As suggested above, the first agent may comprise a single compound or more than one compound that alters the replication rate of a pathogen.

The first agent may be administered as a pharmaceutical formulation comprising one, two, three, four or more compounds that alters the replication rate of a pathogen. When two or more compounds are administered, they may be contained in the same formulation or separate formulations. Pharmaceutical formulations may comprise pharmaceutically acceptable carriers and/or diluents that are commonly known in the art.

The second agent may be any compound or compounds that have anti-infective activity on a pathogen. Thus, for example, if the pathogen is a bacteria, the second agent is one or more compounds that have antibacterial activity, such as an antibiotic. If the pathogen is a virus, the second agent is one or more compounds that have antiviral activity. If the pathogen is a fungus, the second agent is one or more compounds that have antifungal activity. Preferably, the anti-infective activity is inhibition by a percentage of at least about 10, 15, 20, 25, 30, 35, 40, 45, 50, 55, 60, 65, 70, 75, 80, 85, 90, or 95, or more compared to a subject that is not exposed to the second agent. Examples of antibiotics include, but are not limited to, a glycopeptide, a rifamycin, a sulfonamide, a beta-lactam, a tetracycline, an amphenicol (such as chloramphenicol), an aminoglycoside, a macrolide, a streptogramin, a quinolone, a fluoroquinolone, an oxazolidinone and a lipopeptide. Specific examples of antibiotics include, but are not limited to, tetracycline, tigecycline, minocycline, oxazolidinone antibacterial agents, aminoglycoside antibacterial agents, quinolone antibacterial agents, vancomycin, teicoplanin, eremomycin, oritavancin, chloroeremomycin, and daptomycin.

As suggested above, the second agent may comprise one or more anti-infective compounds. In addition to the one or more anti-infective compounds, the second agent may also comprise one or more compounds that augment the activity of the anti-infective compounds. Such augmentation is achieved via compounds that increase the activity or effectiveness of an anti-infective compound (e.g., alter the pharmacokinetics and/or pharmacodynamics of an anti-infective compound), compounds that target an anti-infective compound to a particular location in the subject, and compounds that target an anti-infective compound to a particular pathogen, to name a few non-limiting examples.

The second agent may be administered as a pharmaceutical formulation comprising one, two, three, four or more anti-infectives, and optionally one or more compounds that augment the activity of the anti-infective compounds. When two or more compounds are administered, they may be contained in the same formulation or separate formulations. Pharmaceutical formulations may comprise pharmaceutically acceptable carriers and/or diluents that are commonly known in the art.

The infectious disease may be a bacterial infection, a viral infection or a fungal infection.

It will be clear to the skilled artisan that the bacterial infection is not particularly limited and includes such bacterial infection as pulmonary infections (including infections in the lungs of subjects with cystic fibrosis and ventilator-associated pneumonia), skin and skin structure infections (including burns, wounds, and infections of surgical sites), blood infections (including sepsis), urinary tract infections, infections of the eye or ear, bacterial vaginosis, bacterial meningitis, and bacterial gastroenteritis. Specific examples of bacterial infections include, but are not limited to, otitis media, a urinary tract infection, a skin and skin-structure infection, pneumonia, endocarditis, a bone and/or joint infection, an infection associated with a biofilm, tuberculosis, or leprosy. The source of the infection is also unlimited and includes hospital-acquired (nosocomial) and community-acquired infections.

Examples of viral infections include, but are not limited to, Skin vesicles, mucosal ulcers, aseptic meningitis, rabies, encephalitis, poliomyelitis, mumps, measles, post-infectious encephalomyelitis, Kaposi sarcoma, multicentric Castleman disease, primary effusion lymphoma, influenza, Reye syndrome, infectious mononucleosis, Cytomegalic inclusion disease, Burkitt's lymphoma, Hodgkin's lymphoma, nasopharyngeal carcinoma, hyperplastic epithelial lesions, cervical carcinoma, squamous cell carcinomas, herpes labialis, cold sores, gingivostomatiti, tonsillitis, pharyngitis, keratoconjunctivitis, hand, foot and mouth disease, pleurodynia, aseptic meningitis, pericarditis, myocarditis, gastroenteritis, keratoconjunctivitis, pharyngitis, croup, pharyngoconjunctival fever, pneumonia, cystitis, croup, bronchiolitis, common cold, congenital rubella, German measles, chickenpox, herpes zoster, congenital varicella syndrome, influenza-like syndrome, severe bronchiolitis with pneumonia, acquired immune deficiency syndrome, acute hepatitis, chronic hepatitis, hepatic cirrhosis, and hepatocellular carcinoma.

Examples of fungal infections include, but are not limited to, allergic disease, meningitis, meningo-encephalitis, histoplasmosis, pneumonia, and respiratory disease.

The pathogen may be a bacterium, a virus, or a fungus.

Examples of bacteria include, but are not limited to, a mycobacterium, a species of staphylococci, a species of streptococci, or a Gram-negative bacilli. Specific examples include, but are not limited to, *Actinomyces israelii, Bacillus anthracis, Bacillus cereus, Bartonella henselae, Bartonella quintana, Bordetella pertussis, Borrelia burgdorferi, Borrelia Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Enterococcus faecalis, Enterococcus faecium, Escherichia coli, Francisella tularensis, Haemophilus influenza, Helicobacter pylori, Klebsiella pneumoniae, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitides, Nocardia asteroids, Pseudomonas aeruginosa, Rickettsia rickettsia, Salmonella typhi, Salmonella typhimurium, Shigella sonnei, Shigella dysenteriae, Staphylococcus aureus, Staphylococcus epidermidis, Staphylococcus saprophyticus, Streptococcus agalactiae, Streptococcus pneumoniae, Streptococcus pyogenes, Streptococcus viridans, Treponema pallidum, Ureaplasma urealyticum, Vibrio cholera, Yersinia pestis, Yersinia enterocolitica,* and *Yersinia pseudotuberculosis*. Specific examples also include *Mycobacterium tuberculosis, M. leprae, Staphylococcus aureus, Streptococcus pneumoniae,* and *Escherichia coli.*

Examples of virus include, but are not limited to, viruses from the following families: Adenoviridae, Herpesviridae, Papillomaviridae, Polyomaviridae, Poxviridae, Hepadnaviridae, Parvoviridae, Astroviridae, Caliciviridae, Picornaviridae, Coronaviridae, Flaviviridae, Togaviridae, Hepeviridae, Retroviridae, Orthomyxoviridae, Arenaviridae, Bunyaviridae, Filoviridae, Paramyxoviridae, Rhabdoviridae and Reoviridae.

Examples of fungi include, but are not limited to, *Candida species, Aspergillus fumigatus, Aspergillus flavus, Cryptococcus neoformans, Cryptococcus laurentii, Cryptococcus albidus, Cryptococcus gattii, Histoplasma capsulatum, Pneumocystis jirovecii, Pneumocystis carinii,* and *Stachybotrys chartarum.*

The skilled artisan will understand that in view of the underlying basis for the invention, the identity of the infectious disease and the pathogen can vary widely. However, both the infectious disease and the pathogen will generally be associated with infectious diseases that typically require days (e.g., more than about 1, 2, 3, 4, 5, 6, 7, 8, 9, or 10, or more), weeks (e.g., more than about 1, 2, 3, 4, 5, 6, 7, 8, 9, or 10, or more), or months (e.g., more than about 1, 2, 3, 4, 5, 6, 7, 8, 9, or 10, or more) in which to achieve treatment in the absence of the first agent that alters the replication rate of the pathogen.

In each aspect of the invention, the subject is human, a non-human primate, bird, horse, cow, goat, sheep, a dog, cat, or rodent.

The methods of the present invention are not limited in the timing or manner in which the first and second agents are administered to a subject having an infectious disease. For example, and with respect to timing, the first and second agents may be administered to a subject sequentially or concurrently. When administered sequentially, the agents may be administered in either order, and administration may be separated in time by minutes or hours or days. When administered concurrently, the timing and duration of administration may be identical or may only overlap for a portion of the time over which the agents are being administered. The first and second agents may be administered in the same pharmaceutical formulation or the agents may be administered in separate pharmaceutical formulations. The agents may be administered by the same physical means or different means, and also may be administered to the same locus in the subject or different loci.

Each of the agents may be individually administered to a subject once or more than once, such as one, two, three or four times a day, on a daily basis, every other day, every third day, every fourth day, every fifth day, every sixth day, once a week, or less frequently.

As used herein, "treating" and "treatment" can mean complete eradication of the pathogen from the subject. Complete eradication means the failure of the pathogen to be detected in a biological sample (e.g., blood, urine, stool, mucous, saliva) through testing typically undertaken to determine whether a subject is infected by a particular pathogen. However, "treating" and "treatment" also includes a decrease in symptoms of the infectious disease by a percentage of at least about 100, 95, 90, 85, 80, 75, 70, 65, 60, 55, 50, 45, 40, 35, 30, 25, 20, 15, 10, or 5, in comparison to a subject that has not received treatment for the infectious disease, as judged, for example, by an attending physician.

As used herein, "shortening" means a decrease in the duration of infectious disease treatment in a subject, in comparison to a subject to which the same treatment is administered but in the absence of the first agent. The decrease in duration may be a matter of minutes (such as 15, 30, 45, 60 or more minutes), hours (such as 4, 8, 12, 16, 20, 24 or more hours), days (such as 1, 2, 3, 4, 5, 6, 7 or more days) or weeks (such as 1, 2, 3, 4 or more weeks).

As used herein, "increasing" means an increase of at least 10, 20, 30, 40, 50, 60, 70 80, 90, 95 percent, or more, in the effectiveness of an anti-infective in treatment of an infectious disease in a subject, in comparison to a subject to which the same treatment is administered but in the absence of the first agent. Effectiveness may be, for example, the amount of pathogen killing or inactivation, the speed of pathogen killing or inactivation, or the activity of the second agent.

The invention also provides a kit comprising one or more containers filled with one or more first agent and one or more second agent. The kit may also include instructions for use. Associated with the kit may further be a notice in the form prescribed by a governmental agency regulating the manufacture, use or sale of pharmaceuticals or biological products, which notice reflects approval by the agency of manufacture, use or sale for human administration.

EXAMPLE 1

Figure 2:
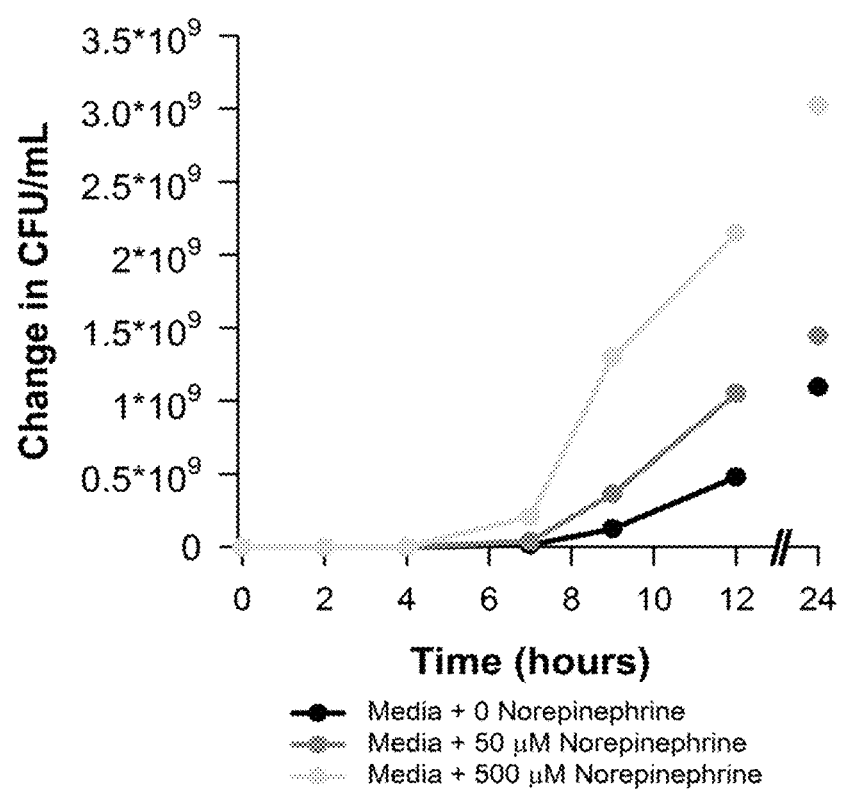
FIG. 2 shows the impact of norepinephrine concentration on *E. coil* JMI 21711R growth rate.

FIG. 1 shows the impact of sodium chloride concentration on the change in bacterial density (starting inoculum [time 0], $1\times10^6$ CFU/mL) in vitro over 24 hours for *S. aureus* ATCC 29213. Note that as sodium chloride concentration increases, the bacterial replication rate decreases. Similarly, FIG. 2 shows the impact of norepinephrine on the change in bacterial density (starting inoculum [time 0], $1\times10^6$ CFU/mL) in vitro over 24 hours for *E. coli* JMI 21711R. Note that as norepinephrine concentration increases so too does the bacterial replication rate.

EXAMPLE 2

Figure 3:
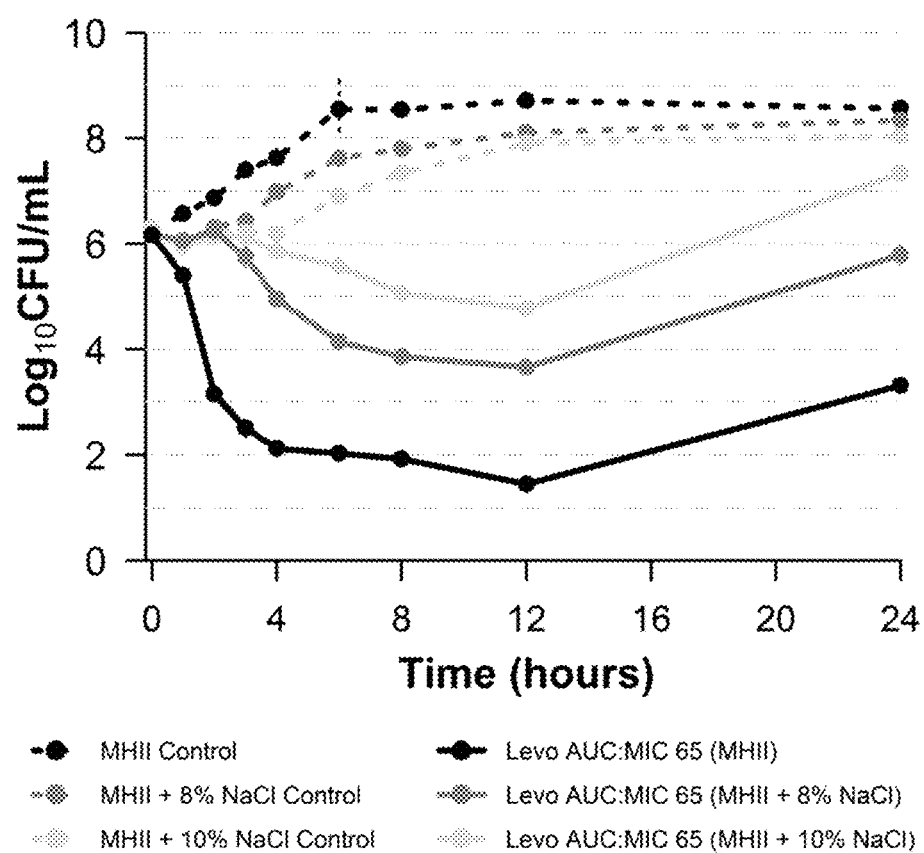
FIG. 3 shows the impact of sodium chloride concentration on rate and extent of levofloxacin bactericidal activity against *S. aureus* ATCC 29213 in a 24-hour one-compartment in vitro infection model.

Not previously recognized is the potential to modulate the intrinsic bacterial replication rate in combination with an antimicrobial agent as a means to increase the rate and extent of bactericidal activity. To this end, slowing of the intrinsic bacterial growth rate in the context of an antimicrobial exposure was found to reduce the bactericidal effect of the antimicrobial agent. More specifically, in a 24-hour one-compartment dynamic in vitro infection model *S. aureus* ATCC 29213 (levofloxacin MIC, 0.125 mg/L) was exposed to a clinically-effective levofloxacin exposure (free-drug AUC:MIC ratio, 65; administered as a single dose). Each treatment arm and associated control arm differed only in sodium chloride concentration (0, 8, and 10%) within the growth media. FIG. 3 shows the impact of sodium chloride concentration on the change in bacterial density in vitro over the study period relative to no-treatment control arm. Note that as the sodium chloride concentration increases, the rate (slope, 0-4 hours) and extent (24-hour CFU/mL) decreased over the study period. Note also that bacterial killing occurred only during bacterial replication. For instance, the 0% sodium chloride control arm grew immediately and there was an immediate CFU/mL reduction in the corresponding active treatment arm. In contrast, the growth was delayed for four hours in the 10% sodium chloride control arm and there was a similar delay in CFU/mL reduction in the corresponding active treatment arm.

To confirm that this observation was not due to sodium chloride altering levofloxacin bactericidal effect, *S. aureus* ATCC 29213 was plated on Muller-Hinton agar supplemented with 0, 8, and 10% sodium chloride and exposed the bacterium to a range of levofloxacin concentrations (0.5 to 5 mg/L). The resultant zones of inhibition did not vary by sodium chloride concentration (data not shown), indicating that the relationship between increasing sodium chloride concentration and decreasing bacterial replication rate was not due to an alteration of levofloxacin bactericidal effect.

Figure 4:
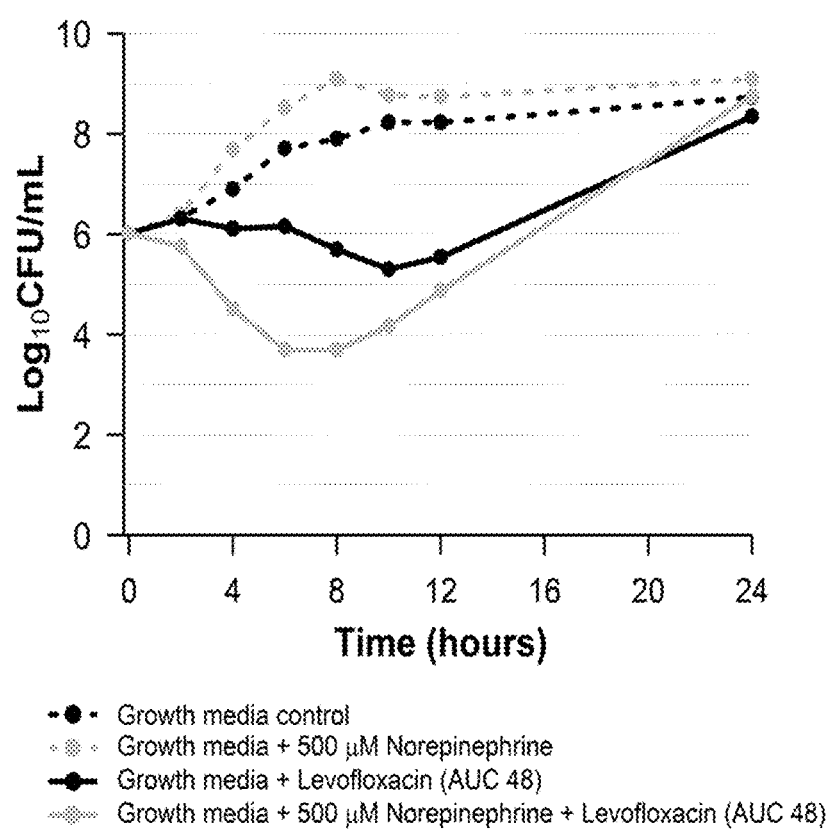
FIG. 4 shows the impact of norepinephrine (500 μM) on rate and extent of levofloxacin bactericidal activity against *E. coli* JMI 21711R in a 24-hour one-compartment in vitro infection model.

Similarly, it was found that increasing the intrinsic bacterial growth rate in the context of an antimicrobial exposure increases the bactericidal effect of the antimicrobial agent. In a 24-hour one-compartment in vitro infection model *E. coli* JMI 21711R (levofloxacin MIC, 8 mg/L) was exposed to a typical levofloxacin exposure (free-drug AUC 48) following a 500 mg once-daily dose (AUC:MIC ratio, 6). Each treatment arm and its associated control arm differed only in norepinephrine concentration (0, 500 µM) within the growth media. FIG. 4 shows the impact of norepinephrine on the change in bacterial density in vitro over the study period relative to no-treatment control arm. First, note that the no-treatment control arm grew well but the norepinephrine-containing control arm grew faster. Second, note that the rate (slope, 0-4 hours) and extent (24-hour CFU) of cell kill was greater in the norepinephrine-levofloxacin treatment arm than that for levofloxacin alone. The regrowth in norepinephrine-levofloxacin treatment arm was due to amplification of a drug-resistant bacterial subpopulation.

These data significantly built upon the initial observations. That is, the initial studies in a test-tube showed the bacterial replication rate could be slowed by the addition of sodium chloride (FIG. 1) and sped up by norepinephrine (FIG. 2); these preliminary dynamic infection model studies (FIGS. 3 and 4) not only confirmed the initial findings but also showed that speeding up bacterial replication rate increased the rate and extent of bactericidal effect.

EXAMPLE 3

It was also found that slowing the intrinsic bacterial growth rate in the context of an antimicrobial exposure reduces the bactericidal effect of the antimicrobial agent and increases the time-to-event. More specifically, in a 10-day hollow-fiber in vitro infection model system *S. aureus* ATCC 29213 was exposed to a clinically-effective levofloxacin exposure (free-drug AUC, 65; MIC, 0.125 mg/L; AUC:MIC ratio, 520). The treatment arms and associated control arms differed only in sodium chloride concentration (0 and 8%) within the growth media. The initial bacterial inoculum in the model was $1\times10^8$ CFU/mL was selected to approximate that observed in high-density infections, such as pneumonia. Moreover, the 10-day study duration was selected to approximate that typical for pneumonia.

Figure 5:
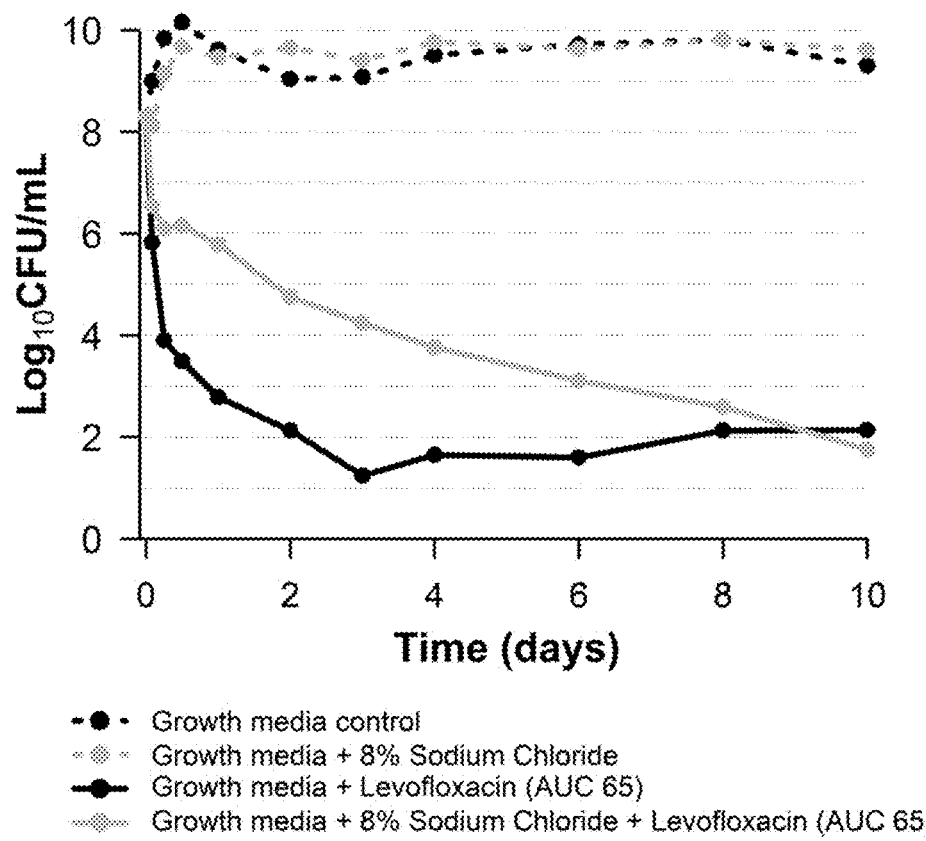
FIG. 5 shows the impact of sodium chloride (8%) on the rate and extent of levofloxacin bactericidal activity against *S. aureus* ATCC 29213 in a hollow-fiber infection model.

FIG. 5 shows the impact of sodium chloride concentration on the change in bacterial density in vitro over the study period. Note that in the media in which the challenge isolate grew slowly (sodium chloride 8%), the time-until a reduction of bacterial density to $1\times10^2$ CFU/mL was 10 days. On the other hand, in the media in which the challenge isolate grew rapidly (sodium chloride 0%), the time-until reduction of bacterial density to $1\times10^2$ CFU/mL was 3 days.

In total, these data build further upon the earlier observations. That is, like in the test-tube and in 24-hour preliminary dynamic infection model studies, bacterial replication rate modulation impacts the rate and extent of bactericidal effect but in a long-term experiment. Further, these data support the notion that an increased bacterial replication rate may result in decreased therapy duration, as evidenced by the 70% reduction in time-until a reduction of bacterial density to $1 \times 10^2$ CFU/mL in "fast" (sodium chloride 0%) versus "slow" (sodium chloride 8%) growing media.

EXAMPLE 4

Figure 6:
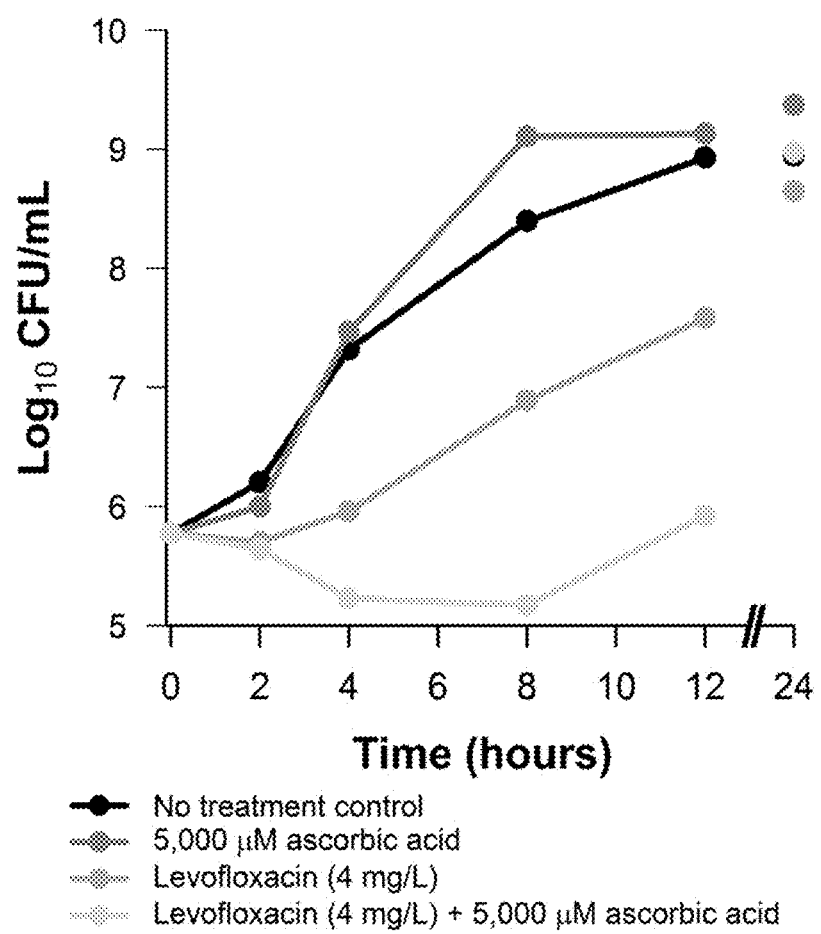
FIG. 6 shows the impact of ascorbic acid with and without levofloxacin on *E. coli* JMI 21711R growth rate.

FIG. 6 shows the impact of ascorbic acid concentration with and without levofloxacin on the change in bacterial density in vitro over 24 hours for *E. coli* JMI 21711R. Note ascorbic acid increases the bacterial replication rate relative to no treatment control. Moreover, note the impact of ascorbic acid on the time-course of levofloxacin antimicrobial activity.

While the invention has been described with reference to certain particular embodiments thereof, those skilled in the art will appreciate that various modifications may be made without departing from the spirit and scope of the invention. The scope of the appended claims is not to be limited to the specific embodiments described.

What is claimed is:

1. A method of treating a bacterial infection in a subject, comprising administering to a subject having a bacterial infection (i) a first agent that increases the replication rate of a bacterium causing the infection and (ii) a second agent that is an anti-infective against the bacterium causing the infection, wherein the second agent comprises one or more antibiotics, and wherein the bacterium causing the infection is a mycobacterium, a species of staphylococci, a species of streptococci, or a Gram-negative bacilli.

2. A method of shortening duration of treatment of a bacterial infection in a subject, comprising administering to a subject having a bacterial infection (i) a first agent that increases the replication rate of a bacterium causing the infection and (ii) a second agent that is an anti-infective against the bacterium causing the infection, wherein the second agent comprises one or more antibiotics, and wherein the bacterium causing the infection is a mycobacterium, a species of staphylococci, a species of streptococci, or a Gram-negative bacilli.

3. A method of increasing effectiveness of treatment of a bacterial infection in a subject, comprising administering to a subject having a bacterial infection (i) a first agent that increases the replication rate of a bacterium causing the infection and (ii) a second agent that is an anti-infective against the bacterium causing the infection, wherein the second agent comprises one or more antibiotics, and wherein the bacterium causing the infection is a mycobacterium, a species of staphylococci, a species of streptococci, or a Gram-negative bacilli.

4. The method of claim 1, wherein the first agent is one or more compounds comprising an aromatic ring with two adjacent hydroxyl groups.

5. The method of claim 4, wherein the aromatic ring with two adjacent hydroxyl groups is a catechol moiety.

6. The method of claim 4, wherein the aromatic ring with two adjacent hydroxyl groups is a 3,4-dihydroxyfuran moiety.

7. The method of claim 4, wherein the one or more compounds is a catecholamine.

8. The method of claim 1, wherein the first agent is one or more compounds selected from the group consisting of Dopamine, Norepinephrine, Nordefrin, Levodopa, Levonordefrin (Corbadrine), Methyldopa, Isoetharine, Isoproterenol, Carbidopa, Epinephrine, Methyldopate, Dobutamine, Droxidopa and Ascorbic Acid.

9. The method of claim 1, wherein the one or more antibiotics are selected from the group consisting of a glycopeptide, a rifamycin, a sulfonamide, a beta-lactam, a tetracycline, an amphenicol, an aminoglycoside, a macrolide, a streptogramin, a quinolone, a fluoroquinolone, an oxazolidinone and a lipopeptide.

10. The method of claim 9, wherein the amphenicol is chloramphenicol.

11. The method of claim 1, wherein the one or more antibiotics are selected from the group consisting of tetracycline, tigecycline, minocycline, oxazolidinone antibacterial agents, aminoglycoside antibacterial agents, quinolone antibacterial agents, vancomycin, teicoplanin, eremomycin, oritavancin, chloroeremomycin, and daptomycin.

12. The method of claim 1, wherein the first agent and the second agent are administered to the subject sequentially or concurrently, and when administered sequentially the agents may be administered in either order.

13. The method of claim 1, wherein the bacterial infection is otitis media, a urinary tract infection, a skin and skin-structure infection, pneumonia, endocarditis, a bone and/or joint infection, an infection associated with a biofilm, tuberculosis, or leprosy.

14. The method of claim 1, wherein the bacterium causing the infection is *Mycobacterium tuberculosis, M. leprae, Staphylococcus aureus, Streptococcus pneumoniae*, or *Escherichia coli*.

15. The method of claim 1, wherein the subject is human, a non-human primate, bird, horse, cow, goat, sheep, a dog, cat, or rodent.

16. A method of treating a bacterial infection in a subject, comprising administering to a subject having a bacterial infection (i) a first agent that increases the replication rate of a bacterium causing the infection and (ii) a second agent that is an anti-infective against the bacterium causing the infection, wherein the first agent is one or more compounds selected from the group consisting of Dopamine, Norepinephrine, Nordefrin, Levodopa, Levonordefrin (Corbadrine), Methyldopa, Isoetharine, Isoproterenol, Carbidopa, Epinephrine, Methyldopate, Dobutamine, Droxidopa and Ascorbic Acid, and wherein the second agent is one or more antibiotics selected from the group consisting of tetracycline, tigecycline, minocycline, oxazolidinone antibacterial agents, aminoglycoside antibacterial agents, quinolone antibacterial agents, vancomycin, teicoplanin, eremomycin, oritavancin, chloroeremomycin, and daptomycin, and wherein the bacterium causing the infection is a mycobacterium, a species of staphylococci, species of streptococci, or a Gram-negative bacilli.

17. A method of treating a bacterial infection in a subject, comprising administering to a subject having a bacterial infection (i) a first agent that increases the replication rate of a bacterium causing the infection and (ii) a second agent that is an anti-infective against the bacterium causing the infection, wherein the second agent comprises one or more antibiotics, and wherein the bacterial infection is otitis media, a urinary tract infection, a skin and skin-structure infection, pneumonia, endocarditis, a bone and/or joint infection, an infection associated with a biofilm, tuberculosis, or leprosy.

18. The method of claim 17, wherein the bacterium causing the infection is a mycobacterium, a species of staphylococci, a species of streptococci, or a Gram-negative bacilli.

19. The method of claim 17, wherein the bacterium causing the infection is *Mycobacterium tuberculosis, M. leprae, Staphylococcus aureus, Streptococcus pneumoniae,* or *Escherichia coli.*

20. The method of claim 2, wherein the bacterium causing the infection is *Mycobacterium tuberculosis, M. leprae, Staphylococcus aureus, Streptococcus pneumoniae,* or *Escherichia coli.*

21. The method of claim 3, wherein the bacterium causing the infection is *Mycobacterium tuberculosis, M. leprae, Staphylococcus aureus, Streptococcus pneumoniae,* or *Escherichia coli.*

22. The method of claim 2, wherein the first agent is one or more compounds selected from the group consisting of Dopamine, Norepinephrine, Nordefrin, Levodopa, Levonordefrin (Corbadrine), Methyldopa, Isoetharine, Isoproterenol, Carbidopa, Epinephrine, Methyldopate, Dobutamine, Droxidopa and Ascorbic Acid.

23. The method of claim 3, wherein the first agent is one or more compounds selected from the group consisting of Dopamine, Norepinephrine, Nordefrin, Levodopa, Levonordefrin (Corbadrine), Methyldopa, Isoetharine, Isoproterenol, Carbidopa, Epinephrine, Methyldopate, Dobutamine, Droxidopa and Ascorbic Acid.

* * * * *